US012773413B2

(12) United States Patent
Vincent et al.

(10) Patent No.: US 12,773,413 B2
(45) Date of Patent: Oct. 27, 2026

(54) PHARMACEUTICAL HYDROCORTISONE SOLUTION FOR INJECTION DEVICE

(71) Applicant: CROSSJECT, Dijon (FR)

(72) Inventors: Laurette Vincent, Dijon (FR); Olivier Lacombe, Talant (FR); Marion Iguiniz, Quetigny (FR)

(73) Assignee: CROSSJECT, Dijon (FR)

( * ) Notice: Subject to any disclaimer, the term of this patent is extended or adjusted under 35 U.S.C. 154(b) by 356 days.

(21) Appl. No.: 18/702,934

(22) PCT Filed: Nov. 8, 2022

(86) PCT No.: PCT/EP2022/081164
§ 371 (c)(1),
(2) Date: Apr. 19, 2024

(87) PCT Pub. No.: WO2023/083825
PCT Pub. Date: May 19, 2023

(65) Prior Publication Data

US 2024/0408110 A1 Dec. 12, 2024

(30) Foreign Application Priority Data

Nov. 9, 2021 (FR) ..................................... 21/11880

(51) Int. Cl.
*A61K 31/573* (2006.01)
*A61K 9/00* (2006.01)
(Continued)

(52) U.S. Cl.
CPC .......... *A61K 31/573* (2013.01); *A61K 9/0019* (2013.01); *A61K 9/08* (2013.01); *A61K 47/20* (2013.01); *A61M 5/30* (2013.01)

(58) Field of Classification Search
CPC ...... A61K 31/573; A61K 9/0019; A61K 9/08; A61K 47/20
See application file for complete search history.

(56) References Cited

U.S. PATENT DOCUMENTS 3,696,195 A 10/1972 Crivellaro et al.
2014/0296191 A1 10/2014 Patel et al.
(Continued)

FOREIGN PATENT DOCUMENTS

FR 2051504 A1 4/1971
FR 2 807 946 A1 10/2001
(Continued)

OTHER PUBLICATIONS

Feb. 1, 2023 International Search Report issued in International Patent Application No. PCT/EP2022/081164.
(Continued)

*Primary Examiner* — Dung T Ulsh
(74) *Attorney, Agent, or Firm* — Oliff PLC

(57) ABSTRACT

A pharmaceutical solution of hydrocortisone includes in mg per 1 mL of solution: between 150 mg and 170 mg of hydrocortisone or a pharmaceutically acceptable salt thereof in equivalent amount, between 2 mg and 7.5 mg of monothioglycerol, and Qsp 1 mL of solvent. The solution is used in the treatment of acute adrenal insufficiency and asthma and concerns an injection kit including an injection device and this pharmaceutical solution.

12 Claims, 4 Drawing Sheets

(51) Int. Cl.
*A61K 9/08* (2006.01)
*A61K 47/20* (2006.01)
*A61M 5/30* (2006.01)

(56) References Cited

U.S. PATENT DOCUMENTS

2019/0314273 A1 10/2019 Bardonnaud et al.
2022/0096496 A1* 3/2022 Chen ........................ A61K 9/08

FOREIGN PATENT DOCUMENTS

FR 2 815 544 A1 4/2002
FR 3 057 775 A1 4/2018
WO 95/06112 A1 3/1995

OTHER PUBLICATIONS

May 2, 2024 International Preliminary Report on Patentability issued in International Patent Application No. PCT/EP2022/081164.
George Derringer et al. "Simultaneous Optimization of Several Response Variables". Journal of Quality Technology, 1980, vol. 12, No. 4, pp. 214-219.

* cited by examiner

[Fig. 1]
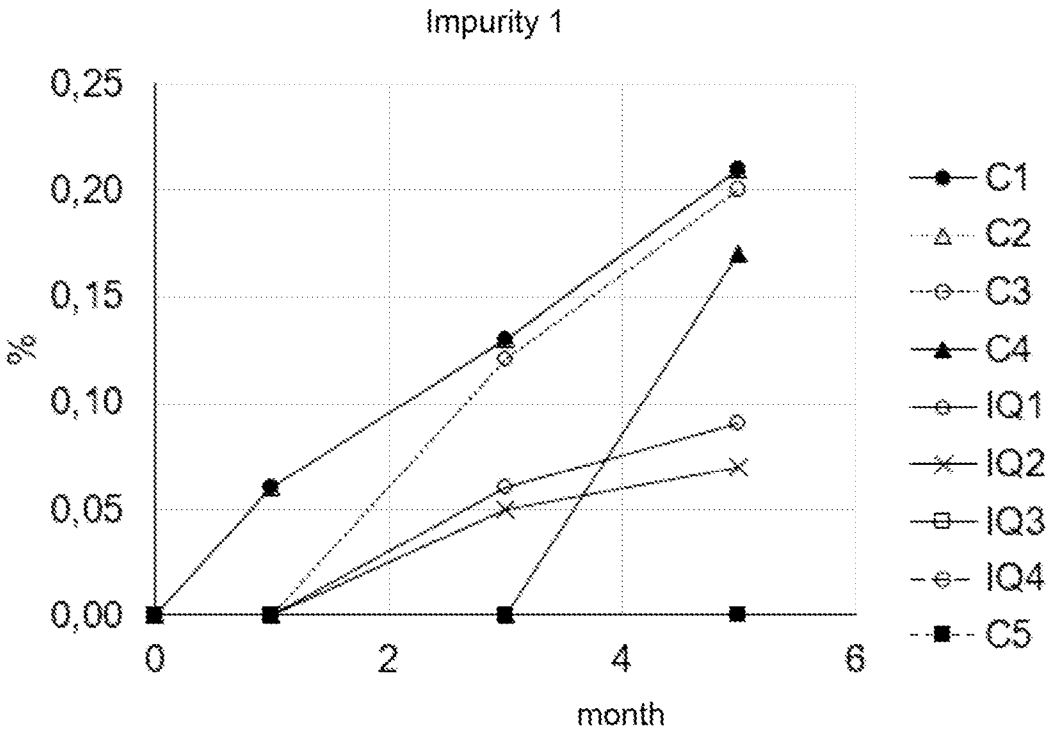
[Fig. 2]
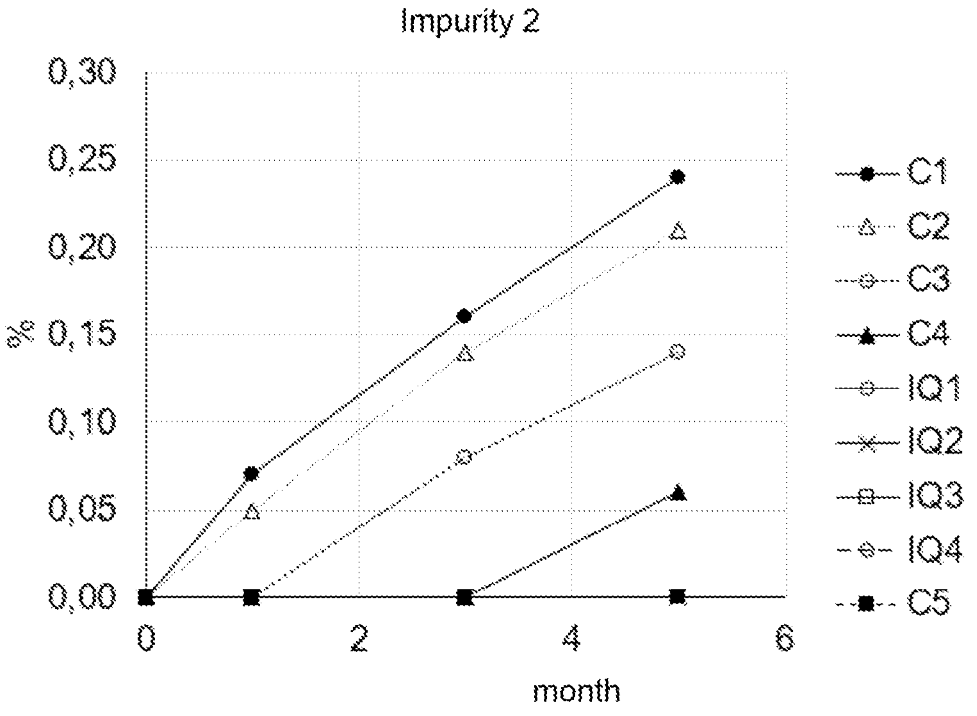

[Fig. 3]
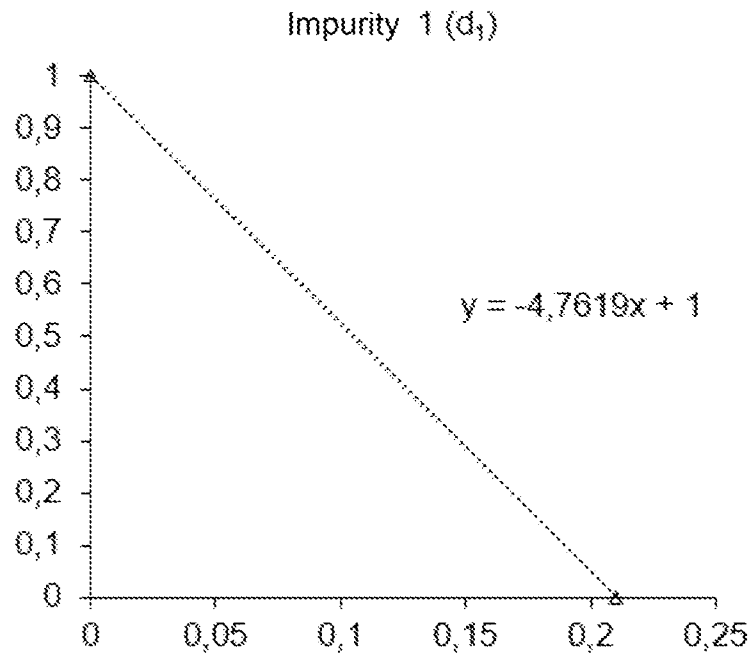
[Fig. 4]
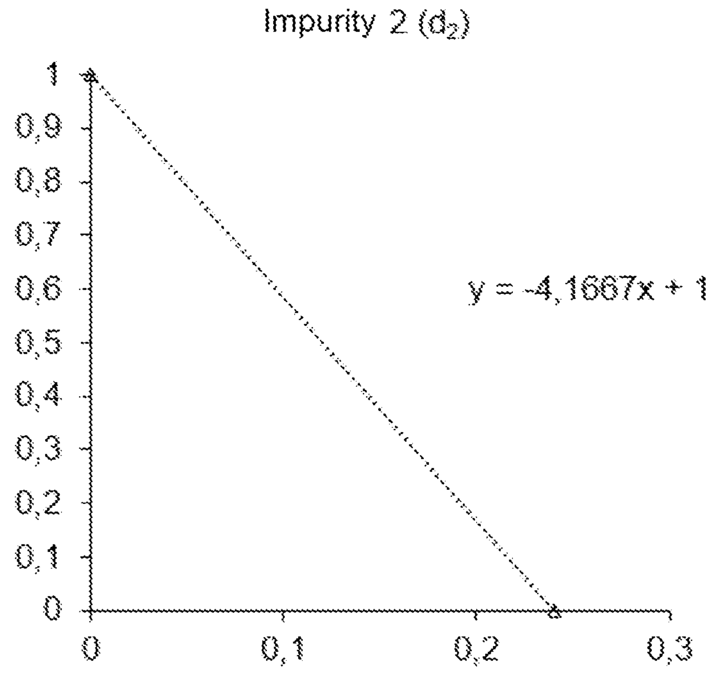

[Fig. 5]
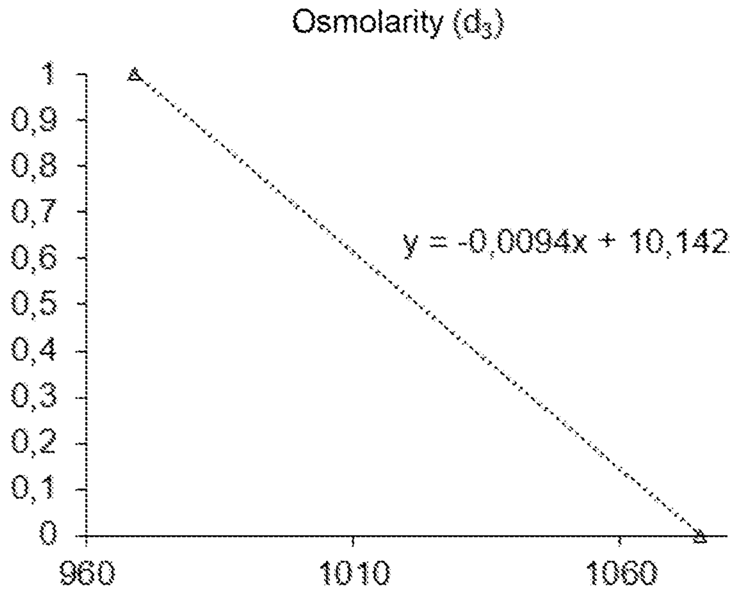
[Fig. 6]
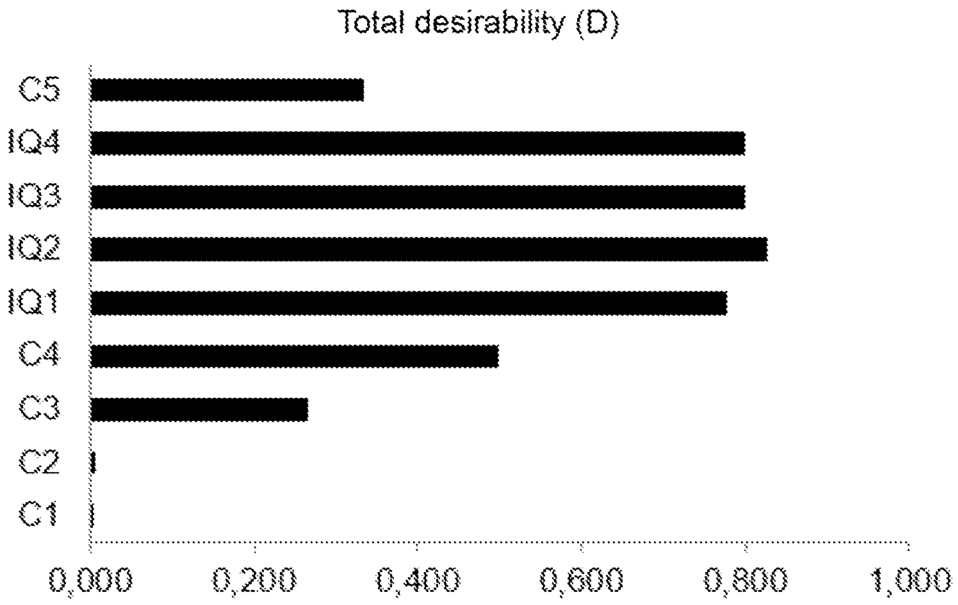

[Fig. 7]
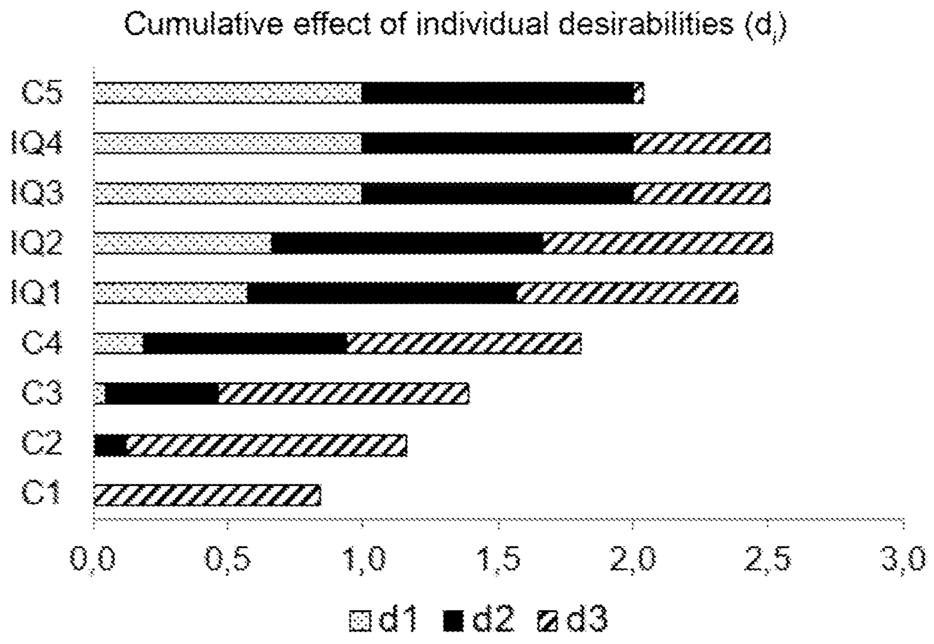

PHARMACEUTICAL HYDROCORTISONE SOLUTION FOR INJECTION DEVICE

The invention concerns a pharmaceutical solution of hydrocortisone or a salt pharmaceutically acceptable thereof (hereinafter abbreviated «pharmaceutical hydrocortisone solution») intended to be injected parenterally, in particular intramuscularly.

The hydrocortisone and the hydrocortisone salts are known to be used as anti-inflammatory agents. It is common to use these active substances in the treatment in particular of asthma, endocrine disorders, dermatological disorders and allergic conditions, as well as acute adrenal insufficiency.

The hydrocortisone and its salts belong to the family of corticosteroids.

The hydrocortisone, as well as its salts, are sensitive to oxidation. This is why pharmaceutical solutions of these active substances always comprise at least one antioxidant.

For example, the pharmaceutical product marketed by the company AMDIPHARM under the trade name Efcortesol® is known which is a pharmaceutical solution of hydrocortisone sodium phosphate at a concentration of 13.39% m/v (in other words there is a 13.39 g of this salt in 100 mL of solution). This product is packaged either in 1 mL ampoules which contain 100 mg of hydrocortisone, or in 5 mL ampoules which contain 500 mg of hydrocortisone. The Efcortesol® further comprises:

- two antioxidants: the disodium ethylenediaminetetraacetate (hereinafter abbreviated «disodium EDTA») which also has the function of being a chelating agent, and the sodium formaldehyde bisulfite which is also an anti-microbial,
- sodium hydrogen phosphate and sodium dihydrogen phosphate,
- water for injection.

However, the sodium formaldehyde bisulfite does not appear on the GRAS list («GRAS» being the acronym for «Generally Recognized As Safe» of the FDA («FDA» being the acronym for «Food and Drug Administration». Furthermore, this antioxidant is not described in the international reference work as a source of information on the pharmaceutical excipients, which is the «Handbook of pharmaceutical excipients».

Moreover, in order to respect the dose necessary for the therapeutic indication (for example acute adrenal insufficiency, asthma or any disease requiring the rapid and significant intake of a corticosteroid) during an intramuscular injection which implies a lower injected volume, a concentration of the pharmaceutical solution higher than that offered by the pharmaceutical product Efcortesol® may be required.

The dose of hydrocortisone to be injected necessary for the therapeutic indication is generally in the range of 100 mg and taking into account the volumes of pharmaceutical solution that the injection devices can contain (in particular needle-free injection devices with pyrotechnic cartridge) which are approximately 0.6 to 0.7 mL, a pharmaceutical solution containing hydrocortisone at a concentration comprised between 150 and 170 mg/ml or a pharmaceutically acceptable salt thereof in equivalent amount would be perfectly appropriate.

This is why it would be desirable to have a new pharmaceutical solution of hydrocortisone or a pharmaceutically acceptable salt thereof which can be more concentrated than the known solution of Efcortesol® and which is stable over time. It would also be advantageous if said solution presents, as far as possible, a minimum of unknown impurities for which a characterization and a laborious toxicity study would be necessary.

The inventors of the present invention have sought to develop a new pharmaceutical solution of hydrocortisone or a pharmaceutically acceptable salt thereof intended to be injected parenterally, in particular intramuscularly, by substituting the antioxidants of Efcortesol® which are sodium formaldehyde bisulfite and disodium EDTA with another antioxidant appearing in the lists of pharmaceutical excipients in reference works such as the one mentioned above, said solution must:

- be free of unknown impurities in significant quantities which would require a characterization,
- be stable over time and
- present the lowest possible osmolarity.

The inventors of the present invention have discovered that the use of the monothioglycerol antioxidant at a determined concentration in a pharmaceutical solution of hydrocortisone at a concentration comprised between 150 and 170 mg/mL or of a pharmaceutically acceptable salt thereof in equivalent amount made it possible to perfectly achieve all these objectives.

The present invention has as its first object a pharmaceutical solution of hydrocortisone which comprises in mg per 1 mL of said solution at least:

- between 150 mg and 170 mg of hydrocortisone or a pharmaceutically acceptable salt thereof in equivalent amount,
- between 2 mg and 7.5 mg of monothioglycerol,
- Qsp 1 mL of solvent.

«Qsp» is the abbreviation for «sufficient amount for» meaning that the amount of solvent is such that the volume of the solution is completed to 1 mL.

The use of monothioglycerol at a concentration comprised between 2 mg/mL and 7.5 mg/mL gives the hydrocortisone solution perfectly remarkable stability over time.

Furthermore, the monothioglycerol is an excipient authorized by the pharmaceutical administrations.

Finally, it was found that a pharmaceutical solution according to the invention has a very low level of impurities, and this under varied and forced storage conditions (namely temperature and relative humidity).

The present invention therefore lies in the selection of monothioglycerol as an antioxidant at a concentration comprised between 2 mg/mL and 7.5 mg/mL to stabilize a pharmaceutical solution of hydrocortisone.

The pharmaceutically acceptable salt of hydrocortisone may be selected from hydrocortisone sodium phosphate, hydrocortisone sodium succinate, hydrocortisone hydrogen succinate, hydrocortisone butyrate and hydrocortisone acetate.

Preferably, the pharmaceutically acceptable salt of hydrocortisone is the hydrocortisone sodium phosphate.

In an embodiment of the invention, the concentration of hydrocortisone in said pharmaceutical solution is 160 mg/mL.

In an embodiment of the invention, the monothioglycerol concentration is comprised between 2.5 mg/mL and 5 mg/mL.

In an embodiment of the invention, the monothioglycerol concentration is comprised between 5 mg/mL and 7.5 mg/mL.

The solvent can be any pharmaceutically acceptable solvent which is compatible with hydrocortisone and its salts and all the other compounds which comprise said pharmaceutical solution according to the invention. This may be water, particularly water used in the injection devices (in other words water for injection), as well as water containing isotonicity additives or sodium chloride solutions. Water for injection is ultra-pure and free of bacterial contaminants.

The pharmaceutical solution may further comprise at least one buffer. For example, it may be a buffer selected from sodium acetate, sodium citrate, sodium dihydrogen phosphate and sodium hydrogen phosphate.

Preferably, the buffer is a mixture of sodium dihydrogen phosphate and sodium hydrogen phosphate. Quite advantageously, the ratio of the mass of sodium dihydrogen phosphate to the mass of sodium hydrogen phosphate is comprised between 0.03 and 0.06.

In an embodiment of the invention, the concentration of buffer in said solution is comprised between 0.1 mg/ml and 3.5 mg/mL.

The pH of the pharmaceutical solution is advantageously comprised between 7 and 9, preferably between 7.5 and 8.5.

Said pharmaceutical solution may further comprise at least one acceptable pharmaceutical excipient other than monothioglycerol.

In an embodiment of the invention, the pharmaceutical solution comprises in mg per 1 ml of said solution:

- between 210 mg and 220 mg of hydrocortisone sodium phosphate,
- between 2 mg and 7.5 mg, preferably between 2 mg and 5 mg, of monothioglycerol,
- between 0.1 mg and 3.5 mg of at least one buffer,
- Qsp 1 mL of solvent, preferably water for injection.

Preferably, in this embodiment of the invention, the pharmaceutical solution comprises as buffer a mixture of sodium dihydrogen phosphate and sodium hydrogen phosphate whose mass ratio of sodium dihydrogen phosphate on the mass of sodium hydrogen phosphate is comprised between 0.03 and 0.06.

The subject of the present invention is also a method for preparing the pharmaceutical solution according to the invention as described above which comprises at least the following steps:

a) a mixture is prepared with stirring comprising at least the solvent and the monothioglycerol;
b) hydrocortisone or a pharmaceutically acceptable salt thereof is added with stirring so as to obtain said pharmaceutical solution;
c) optionally, at least one filtration step is carried out on the pharmaceutical solution obtained at the end of step b).

If the pharmaceutical solution comprises buffers, these buffers are, preferably before step a), mixed together before being added to the mixture of step a).

When the pharmaceutical solution comprises at least one pharmaceutically acceptable excipient other than monothioglycerol, this excipient can be added to the mixture of step a).

The filtration step may comprise at least one filtration selected from the clarifying filtration and the sterilizing filtration.

Preferably, the filtration step consists of a clarifying filtration followed by a sterilizing filtration.

The invention also relates to the pharmaceutical solution as described above for its use in the treatment of diseases selected from acute adrenal insufficiency, asthma or any disease requiring the rapid and significant intake of a corticosteroid. Preferably, this is the treatment of acute adrenal insufficiency and asthma.

Said solution is advantageously in a form suitable for parenteral, preferably intramuscular administration.

The present invention also relates to an injection kit, preferably an intramuscular injection kit, including:

- an injection device;
- the pharmaceutical solution according to the invention as described above.

Advantageously, the volume delivered by the injection device is comprised between 0.60 mL and 0.65 mL.

Said injection device can be single-use. For example, it comes in a pre-filled tube ready to use.

In a preferred embodiment of the invention, said device is a pre-filled, single-use, needle-free and automatic injection device thanks to a gas generator with which it is equipped. It may be a needle-free injection device with a pyrotechnic cartridge. In this regard, patent applications FR 2 815 544 A1 and FR 2 807 946 A1 describe an example of this injection device.

Quite advantageously, the injection device is a device marketed by the company Crossject under the trade name ZENEO®.

Thus, in an embodiment of the injection kit according to the invention, the injection device is a needle-free injection device with a pyrotechnic cartridge.

The invention will be better understood with the aid of the detailed description which is set out below with reference to the appended drawing representing, by way of non-limiting example, experimental and comparative results of solutions according to the invention.

FIG. 1 is a graph of the content of a first impurity as a function of time for different pharmaceutical solutions according to the invention and comparative solutions.

FIG. 2 is a graph of the content of a 2nd impurity as a function of time for different pharmaceutical solutions according to the invention and comparative solutions.

FIG. 3 is a graph of the desirability function $f_1$ of the criterion $d_1$.

FIG. 4 is a graph of the desirability function $f_2$ of the criterion $d_2$.

FIG. 5 is a graph of the desirability function $f_3$ of the criterion $d_3$.

FIG. 6 is a graph representing the total desirability D for each pharmaceutically tested solution.

FIG. 7 is a graph representing the cumulative desirability value of the 3 criteria $d_1$ to $d_3$ for each of the pharmaceutically tested solution.

EXPERIMENTAL PART

Experiments were carried out in order to compare the physicochemical properties and in particular the impurity content of:

- 4 solutions according to the invention whose hydrocortisone sodium phosphate concentration was 214.7 mg/mL and the monothioglycerol concentration was comprised between 2 mg/ml and 7.5 mg/ml;
- 5 comparative solutions whose hydrocortisone sodium phosphate concentration was 214.7 mg/mL and the monothioglycerol concentration was on the one hand comprised between 0 and 1 mg/ml and on the other hand equal to 10 mg/mL, and finally
- a solution similar to the reference product Efcortesol® with the exception that its hydrocortisone sodium phosphate concentration had been increased and had been set at 214.7 mg/mL, to match the hydrocortisone sodium phosphate concentration of solutions according to the invention and comparative solutions, in order to be under the same test conditions.

Table 1 below details the composition of the solution similar to the product of reference Efcortesol® (hereinafter: «Ref») in mg for 1 ml of said solution.

TABLE 1 detailing the composition of the Efcortesol ® product

| Ingredients | Amount in mg |
|---|---|
| hydrocortisone sodium phosphate | 214.7 |
| sodium hydrogen phosphate | 2.9 |
| sodium dihydrogen phosphate | 0.1 |
| Disodium EDTA | 0.9 |
| sodium formaldehyde bisulfite | 1.7 |
| water | Qsp 1 mL |

Table 2 below details the composition of the 5 comparative solutions (C1 to C5) and the 4 solutions according to the invention (IQ1 to IQ4) in mg per 1 mL of solution.

TABLE 2 detailing the compositions of solutions C1 to C5 and IQ1 to IQ4

| Ingredients | C1 | C2 | C3 | C4 | IQ1 | IQ2 | IQ3 | IQ4 | C5 |
|---|---|---|---|---|---|---|---|---|---|
| Hydrocortisone sodium phosphate | 214.7 | | | | | | | | |
| Sodium hydrogen phosphate | 2.9 | | | | | | | | |
| Sodium dihydrogen phosphate | 0.1 | | | | | | | | |
| monothioglycerol | 0.0 | 0.1 | 0.5 | 1.0 | 2.0 | 2.5 | 5.0 | 7.5 | 10.0 |
| Water | Qsp 1 mL | | | | | | | | |

In all the prepared solutions and as detailed in Tables 1 and 2 above, the hydrocortisone sodium phosphate concentration of 214.7 mg/mL is equivalent to a concentration of 160 mg/mL of hydrocortisone.

All the solutions were obtained in the following manner:

a) a mixture containing sodium dihydrogen phosphate and sodium hydrogen phosphate in water was prepared with stirring, in order to obtain a buffer solution at pH 8.0;

b) the solution obtained in step a) was bubbled;

c) with the exception of solution C1 which was devoid of antioxidant, the antioxidant (namely disodium EDTA and sodium formaldehyde bisulfite for the solution Ref; and monothioglycerol for all other solutions) was added with stirring, and stirring was maintained until the compounds were completely dissolved;

d) hydrocortisone sodium phosphate was then added to the mixture while still stirring, said stirring having been continued until this salt was completely dissolved so as to obtain a solution.

Steps c) and d) were carried out under an insulator swept by a flow of nitrogen.

Nitrogen bubbling is a partial inerting which makes it possible to reduce the contact of the pharmaceutical solution with oxygen and therefore to limit the oxidation of said solution.

The solutions thus obtained were packaged in glass tubes equipped with two caps at their ends.

More precisely, the tubes were filled with 0.65 mL of solution. Nitrogen sweep was applied to the surface of the solutions to remove oxygen present in the headspace of these tubes. Finally, the tubes were closed.

For all the solutions, the pH, the osmolarity and the amount of monothioglycerol were determined at different storage times under a relative humidity of 75% and at a temperature of 40° C.

Moreover, from analyzes by high-performance liquid chromatography (hereinafter abbreviated «HPLC»), the time limits for all the solutions were determined:

- the area percentages of all the impurities present in said solutions; which made it possible to deduce the percentage of purity of said solutions;
- the area percentages of the two impurities (namely «impurity 1» whose relative elution time was 1.26 minutes and «impurity 2» whose relative elution time was 1.29 minutes); which made it possible to deduce the evolution of the content of these 2 impurities in said solutions over time and which is detailed in tables 7 and 8 and represented in FIGS. 1 and 2.

These area percentages are expressed relative to the area of the main peak of the considered solution.

The HPLC analyzes were carried out under the following conditions:

- a column marketed by the company Phenomenex under the trade name Luna® C18 (2) having a particle size of 5 μm and dimensions (250×4.6) mm;
- flow rate of 1.5 mL/minute;
- injection volume of 5 μl;
- ultraviolet detector with variable wavelength comprised between 190 and 400 nm or photodiode detector;
- wavelength of 254 nm;
- column temperature 25° C. (+/−) 2° C.;
- sample at room temperature;
- mobile phase A: 0.1% (v/v) of trifluoroacetic acid in purified water;
- mobile phase B: 0.1% (v/v) trifluoroacetic acid in acetonitrile.

Table 3 below details the composition of the mobile phase as a function of time.

TABLE 3 detailing the composition of the mobile phase as a function of time

| Time (minutes) | Phase A (%) | Phase B (%) |
|---|---|---|
| 0 | 85 | 15 |
| 10 | 85 | 15 |
| 22 | 55 | 45 |
| 38 | 30 | 70 |
| 38.1 | 85 | 15 |
| 43 | 85 | 15 |

Table 4 below details the pH values obtained at t equal to 0, then after 1, 3 and 5 months of storage of the solutions at 40° C. and under a relative humidity of 75%. The initial monothioglycerol contents of said solutions are recalled in Table 4.

These are the numbers in parentheses. «ND» is the abbreviation for «not determined».

TABLE 4

| detailing the pH values | | | | | | | | | | |
|---|---|---|---|---|---|---|---|---|---|---|
| Time | Ref | C1 (0) | C2 (0.1) | C3 (0.5) | C4 (1) | IQ1 (2) | IQ2 (2.5) | IQ3 (5) | IQ4 (7.5) | C5 (10) |
| 0 | 8.07 | 8.22 | 8.21 | 8.20 | 8.14 | 8.12 | 8.12 | 8.16 | 8.12 | 8.09 |
| 1 | 7.98 | 8.08 | 8.07 | 8.09 | 8.11 | 8.09 | 8.08 | 8.05 | 8.04 | 8.03 |
| 3 | 8.00 | 8.05 | 8.06 | 8.09 | 8.06 | 8.06 | 8.01 | 8.03 | 8.02 | 8.04 |
| 5 | ND | 8.04 | 8.05 | 8.06 | 8.07 | 8.03 | 8.04 | 8.04 | 8.01 | 8.05 |

In view of the results detailed in Table 4, it is noted that the pH of all the solutions remains stable over time, despite storage in severe conditions, namely at 40° C. and with a relative humidity of 75%.

Table 5 below details the monothioglycerol content remaining in the solutions C2 to C5 and IQ1 to IQ4 at 1, 3 and 5 months of storage of the solutions at 40° C. and under a relative humidity of 75%. The initial monothioglycerol contents of said solutions are shown in Table 5. These are the numbers in parentheses.

TABLE 5

| detailing the monothioglycerol content | | | | | | | | |
|---|---|---|---|---|---|---|---|---|
| Time | C2 (0.1) | C3 (0.5) | C4 (1) | IQ1 (2) | IQ2 (2.5) | IQ3 (5) | IQ4 (7.5) | C5 (10) |
| 1 | 0 | 0.05 | 0.34 | 1.11 | 1.50 | 3.41 | 5.55 | 6.92 |
| 3 | 0 | 0 | 0.04 | 0.60 | 0.97 | 2.79 | 4.81 | 6.73 |
| 5 | 0 | 0 | 0 | 0.31 | 0.62 | 2.33 | 4.11 | 5.92 |

In view of the results detailed in Table 5, it is noted that for the solutions C2 to C4, the monothioglycerol content decreases during the storage until it completely disappears after 5 months (and from 3 months for the solutions C2 and C3). The reduction or even absence of monothioglycerol in the tested solution results in the generation of impurities and therefore the instability of the tested solution.

Unlike solutions C2 to C4, the solutions according to the invention IQ1 to IQ4 always have a high monothioglycerol content after 5 months under severe storage conditions.

Thus, the monitoring of the evolution of the monothioglycerol content in the solutions tested over time demonstrates that the solutions according to the invention IQ1 to IQ4 are particularly stable in comparison with the comparative solutions C2 to C4.

Table 6 below details the purity percentages of the solutions at t equal to 0, then after 1, 3 and 5 months of storage at 40° C. and under a relative humidity of 75%. The initial monothioglycerol contents of said solutions are recalled in Table 6.

These are the numbers in parentheses.

TABLE 6

| detailing the purity percentages | | | | | | | | | | |
|---|---|---|---|---|---|---|---|---|---|---|
| Time | Ref | C1 (0) | C2 (0.1) | C3 (0.5) | C4 (1) | IQ1 (2) | IQ2 (2.5) | IQ3 (5) | IQ4 (7.5) | C5 (10) |
| 0 | 100 | 100 | 100 | 100 | 100 | 100 | 100 | 100 | 100 | 100 |
| 1 | 99.65 | 99.87 | 99.77 | 99.87 | 99.87 | 99.87 | 99.87 | 99.87 | 99.86 | 99.85 |
| 3 | 99.17 | 99.33 | 99.40 | 99.42 | 99.71 | 99.62 | 99.61 | 99.61 | 99.59 | 99.57 |
| 5 | ND | 98.96 | 98.97 | 99.13 | 99.26 | 99.28 | 99.20 | 99.30 | 99.30 | 99.27 |

In view of the results detailed in Table 6, it is noted that the solutions according to the invention IQ1 to IQ4 present, after 5 months of storage under severe conditions, an excellent purity of about 99.3%.

Table 7 below details the area percentages of the aforementioned impurity 1 at time t equal to 0, then after 1, 3 and 5 months of storage of the solutions at 40° C. and under relative humidity of 75%. The initial monothioglycerol contents of said solutions are recalled in Table 7. These are the numbers in parentheses.

TABLE 7

| detailing the area percentages of the impurity 1 | | | | | | | | | |
|---|---|---|---|---|---|---|---|---|---|
| Time | C1 (0) | C2 (0.1) | C3 (0.5) | C4 (1) | IQ1 (2) | IQ2 (2.5) | IQ3 (5) | IQ4 (7.5) | C5 (10) |
| 0 | 0 | 0 | 0 | 0 | 0 | 0 | 0 | 0 | 0 |
| 1 | 0.06 | 0.06 | 0 | 0 | 0 | 0 | 0 | 0 | 0 |
| 3 | 0.13 | 0.13 | 0.12 | 0 | 0.06 | 0.05 | 0 | 0 | 0 |
| 5 | 0.21 | 0.21 | 0.20 | 0.17 | 0.09 | 0.07 | 0 | 0 | 0 |

FIG. 1 is a graph representing the area percentages of the impurity 1 as a function of the time for each of the solutions.

In view of the results detailed in Table 7 and in view of the evolution of the curves in FIG. 1, it is noted that the solutions according to the invention IQ1 to IQ4 present an area percentage of the impurity 1 well lower than that of comparative solutions C1 to C4.

Table 8 below details the area percentages of the aforementioned impurity 2 at time t equal to 0, then after 1, 3 and 5 months of storage of the solutions at 40° C. and under relative humidity of 75%. The initial monothioglycerol contents of said solutions are shown in Table 8. These are the numbers in parentheses.

TABLE 8

| detailing the area percentages of the impurity 2 | | | | | | | | | |
|---|---|---|---|---|---|---|---|---|---|
| Time | C1 (0) | C2 (0.1) | C3 (0.5) | C4 (1) | IQ1 (2) | IQ2 (2.5) | IQ3 (5) | IQ4 (7.5) | C5 (10) |
| 0 | 0 | 0 | 0 | 0 | 0 | 0 | 0 | 0 | 0 |
| 1 | 0.07 | 0.05 | 0 | 0 | 0 | 0 | 0 | 0 | 0 |
| 3 | 0.16 | 0.14 | 0.08 | 0 | 0 | 0 | 0 | 0 | 0 |
| 5 | 0.24 | 0.21 | 0.14 | 0.06 | 0 | 0 | 0 | 0 | 0 |

FIG. 2 is a graph representing the area percentages of the impurity 2 as a function of time for each of the solutions.

In view of the results detailed in Table 8 and in view of the evolution of the curves in FIG. 2, it is noted that the solutions according to the invention IQ1 to IQ4 do not include impurity 2 unlike the comparative solutions C1 to C4 whose content tends to increase over time.

Table 9 below details the osmolarity (expressed in mOsm) of the solutions tested at t equal to 0, then after 1, 3 and 5 months of storage at 40° C. and under a relative humidity of 75%. The initial monothioglycerol contents of said solutions are recalled in Table 9. These are the numbers in parentheses.

TABLE 9

| detailing the osmolarities of the tested solutions | | | | | | | | | |
|---|---|---|---|---|---|---|---|---|---|
| Time | C1 (0) | C2 (0.1) | C3 (0.5) | C4 (1) | IQ1 (2) | IQ2 (2.5) | IQ3 (5) | IQ4 (7.5) | C5 (10) |
| 0 | 931 | 931 | 947 | 945 | 949 | 968 | 995 | 1028 | 1081 |
| 1 | 976 | 971 | 985 | 975 | 1005 | 990 | 1030 | 1053 | 1088 |
| 3 | 989 | 979 | 989 | 996 | 986 | 1008 | 1046 | 1060 | 1089 |
| 5 | 989 | 969 | 980 | 996 | 992 | 989 | 1025 | 1025 | 1075 |

The main objectives to be achieved in the context of the development of a pharmaceutical solution intended to be injected parenterally are:

1) a good stability over time, a parameter which is directly linked to the presence of impurities whose concentration increases over time;
2) an osmolarity, if possible isotonic, that is to say comprised between 270 and 310 mOsm. If the isotonicity is not achievable, the osmolarity must be as low as possible.

In view of the results detailed in Table 9 above, it is noted that the comparative solution C5 (namely the solution whose monothioglycerol content is 10 mg/mL) has a higher osmolarity than that of the solutions according to the invention IQ1 to IQ4. The osmolarity parameter of the comparative solution C5 is therefore less efficient in comparison with the solutions according to the invention IQ1 to IQ4.

Furthermore, in the context of these experiments, a Derringer desirability function was used in order to identify among the tested solutions the pharmaceutical solutions which best satisfied the objectives 1) and 2) detailed above.

In this regard, the publication entitled «Simultaneous optimization of several response Variables» by George Derringer et al., Journal of quality technology, vol 12, no 4, October 1980, pages 214-219, describes the calculation methodology of this desirability function.

In summary, the Derringer desirability function is a mathematical tool allowing the simultaneous optimization of several variable responses (hereinafter referred to as «criteria»). The use of this mathematical tool is very classic in the field of pharmacy to demonstrate the performance of a pharmaceutical solution which has been developed in order to best satisfy different objectives based on several criteria.

As part of these experiments, there were the following 3 criteria to evaluate:

the area percentage of the impurity 1, hereinafter noted «$d_1$»;

the area percentage of the impurity 2, hereinafter noted «$d_2$»;

the osmolarity, hereinafter noted «$d_3$».

The 1st step consisted of defining the Derringer functions for each of the 3 aforementioned criteria, after 5 months of storage at 40° C. and under a relative humidity of 75%.

The duration of 5 months is an interesting duration, because it represents a time at the end of which impurities, if there must be any in the tested pharmaceutical solution, have had time to be developed under storage conditions at 40° C. and under a relative humidity of 75%.

The values of the criteria $d_1$ to $d_3$ were calculated for each tested solution. To do this, a change of variable was made in order to have, for each evaluated criterion, a desirability value comprised between 0 and 1.

More precisely, for each criterion, the value of 1 was assigned to the value of the considered criterion which was the most satisfactory among all the tested solutions (namely the lowest area percentage of the impurity 1 for criterion $d_1$, the lowest area percentage of the impurity 2 for criterion $d_2$ and the lowest osmolarity for criterion $d_3$). The value of 0 was assigned to the value of the considered criterion which was the least satisfactory among all the tested solutions (namely the highest area percentage of the impurity 1 for the criterion $d_1$, the highest area percentage of the impurity 2 for criterion $d_2$ and the highest osmolarity for the criterion $d_3$).

Tables 10 to 12 below summarize these assigned values from 1 and 0 for the criteria $d_1$ to $d_3$ respectively.

TABLE 10

| for the criterion $d_1$ (% area of the impurity 1) | |
|---|---|
| 0 | 1 |
| 0.21 | 0 |

TABLE 11

| for the criterion $d_2$ (% area of the impurity 2) | |
|---|---|
| 0 | 1 |
| 0.24 | 0 |

TABLE 12

| for the criterion $d_3$ (osmolarity) | |
|---|---|
| 969 | 1 |
| 1075 | 0 |

From these 3 tables, 3 linear desirability functions f1, f2 and f3 were determined for respectively the evaluated criteria $d_1$ to $d_3$.

FIG. 3 is a graph of the desirability function f1 of the criterion $d_1$.

FIG. 4 is a graph of the desirability function f2 of the criterion $d_2$.

FIG. 5 is a graph of the desirability function f3 of the criterion $d_3$.

From the desirability function f1 of the criterion $d_1$, it is calculated for each tested solution its desirability value for said criterion $d_1$.

Table 13 below details for each tested solution the area percentage of the impurity 1 and its desirability value for the criterion $d_1$ which was calculated from the function f1.

| Tested solution | % area of the impurity 1 | Desirability value for the criterion $d_1$ |
|---|---|---|
| C1 | 0.21 | $1.0 \cdot 10^{-6}$ |
| C2 | 0.21 | $1.0 \cdot 10^{-6}$ |
| C3 | 0.2 | 0.048 |
| C4 | 0.17 | 0.190 |
| IQ1 | 0.09 | 0.571 |
| IQ2 | 0.07 | 0.667 |
| IQ3 | 0 | 1 |
| IQ4 | 0 | 1 |
| C5 | 0 | 1 |

From the desirability function f2 of the criterion $d_2$, for each tested solution its desirability value for said criterion $d_2$ was calculated.

Table 14 below details for each tested solution the area percentage of the impurity 2 and its desirability value for the criterion $d_2$ which was calculated from the function f2.

| Tested solution | % area of the impurity 2 | Desirability value for the criterion $d_2$ |
|---|---|---|
| C1 | 0.24 | $1.0 \cdot 10^{-6}$ |
| C2 | 0.21 | 0.125 |
| C3 | 0.14 | 0.417 |
| C4 | 0.06 | 0.750 |
| IQ1 | 0 | 1 |
| IQ2 | 0 | 1 |
| IQ3 | 0 | 1 |
| IQ4 | 0 | 1 |
| C5 | 0 | 1 |

From the desirability function f3 of the criterion $d_3$, for each tested solution its desirability value for said criterion $d_3$ was calculated.

Table 15 below details for each tested solution its osmolarity and its desirability value for the criterion $d_3$ which was calculated from the function f3.

| Tested solution | Osmolarity (mOsm) | Desirability value for the criterion $d_3$ |
|---|---|---|
| C1 | 989 | 0.845 |
| C2 | 969 | 1.033 |
| C3 | 980 | 0.930 |
| C4 | 987 | 0.864 |
| IQ1 | 992 | 0.817 |
| IQ2 | 989 | 0.845 |
| IQ3 | 1025 | 0.507 |
| IQ4 | 1025 | 0.507 |
| C5 | 1075 | 0.037 |

Then, the total desirability «D» which corresponds to the geometric mean of all the desirability values for a tested pharmaceutical solution was calculated. This total desirability D makes it possible to compare the different tested pharmaceutical solutions with each other and to classify them in relation to each other: a tested solution which obtains a high total desirability value D corresponds to a pharmaceutical solution which best satisfies all of the set objectives detailed above.

Table 16 below details the total desirability D for each of the tested pharmaceutical solutions.

| Tested solution | D |
|---|---|
| C1 | $9.5 \cdot 10^{-5}$ |
| C2 | 0.0051 |
| C3 | 0.264 |
| C4 | 0.498 |
| IQ1 | 0.776 |
| IQ2 | 0.826 |
| IQ3 | 0.797 |
| IQ4 | 0.797 |
| C5 | 0.333 |

FIG. 6 is a graph representing the total desirability D of each tested pharmaceutical solution.

Furthermore, FIG. 7 is a graph representing the cumulative desirability value of the 3 criteria $d_1$ to $d_3$ for each of the tested pharmaceutical solutions.

In view of the results detailed in Table 16 and in view of FIGS. 6 and 7, it is noted that the solutions according to the invention IQ1 to IQ4 present the maximum satisfaction of the objectives to be achieved for the development of a pharmaceutical solution, namely a low content of impurities (in this case impurities 1 and 2) and the lowest possible osmolarity. This is not the case for the comparative solutions C1 to C5 for which the total desirability D and the accumulation of individual desirabilities are lower.

Thus, the mathematical tool implementing the Derringer desirability function clearly demonstrates that the selection of a monothioglycerol concentration comprised between 2 and 7.5 mg/ml makes it possible to obtain pharmaceutical solutions of hydrocortisone at a concentration comprised between 150 and 170 mg/mL (or a pharmaceutically acceptable salt thereof in equivalent amount) which are optimized because they perfectly meet the objectives defined above for the development of pharmaceutical solutions which are the stability over time and the lowest possible osmolarity.

It should be noted that this optimization is not observed outside of this interval 2 to 7.5 mg/ml of the monothioglycerol concentration. Indeed, the total desirability D is lower on either side of this interval (namely for the solutions C1 to C4 on the one hand and for the solution C5 on the other hand). The solutions C1 to C4 are not optimized with regard to their impurity contents. The solution C5 is not optimized regarding its osmolarity.

The invention claimed is:

1. A pharmaceutical hydrocortisone solution which comprises in mg per 1 mL of said solution at least:

between 150 mg and 170 mg of hydrocortisone or a pharmaceutically acceptable salt thereof in equivalent amount, between 2 mg and 7.5 mg of monothioglycerol, Qsp 1 mL of solvent, «Qsp» being the abbreviation of «amount sufficient for» meaning that the amount of solvent is such that the volume of the solution is completed to 1 mL.

2. The pharmaceutical solution according to claim 1, wherein the pharmaceutically acceptable salt of hydrocortisone is selected from hydrocortisone sodium phosphate, hydrocortisone sodium succinate, hydrocortisone hydrogen succinate, hydrocortisone butyrate hydrocortisone and hydrocortisone acetate.

3. The pharmaceutical solution according to claim 2, wherein the pharmaceutically acceptable salt of hydrocortisone is hydrocortisone sodium phosphate.

4. The pharmaceutical solution according to claim 1, wherein it further comprises at least one buffer.

5. The pharmaceutical solution according to claim 4, wherein the buffer is selected from sodium acetate, sodium citrate, sodium dihydrogen phosphate and sodium hydrogen phosphate.

6. The pharmaceutical solution according to claim 1, wherein the pH of the pharmaceutical solution is comprised between 7 and 9.

7. The pharmaceutical solution according to claim 1, wherein the concentration of hydrocortisone in said pharmaceutical solution is 160 mg/mL.

8. The pharmaceutical solution according to claim 4, wherein it comprises in mg per 1 mL of said solution:

between 210 mg and 220 mg of hydrocortisone sodium phosphate, between 2 mg and 7.5 mg of monothioglycerol, between 0.1 mg and 3.5 mg, at least one buffer, Qsp 1 mL of solvent.

9. The pharmaceutical solution according to claim 1 for its use in the treatment of acute adrenal insufficiency and asthma.

10. The pharmaceutical solution according to claim 9, wherein said solution is in a form suitable for parenteral administration.

11. An injection kit including:

an injection device;

the pharmaceutical solution according to claim 1.

12. The injection kit according to claim 11, wherein the injection device is a needle-free injection device with a pyrotechnic cartridge.

* * * * *